United States Patent
Takacs

(10) Patent No.: US 12,268,712 B2
(45) Date of Patent: Apr. 8, 2025

(54) PHARMACEUTICAL COMPOSITION FOR POSTPARTUM RECOVERY AND TREATMENT OF PELVIC FLOOR DYSFUNCTION

(71) Applicant: Fempharma Europe, LLC, Budapest (HU)

(72) Inventor: Peter Takacs, Norfolk, VA (US)

(73) Assignee: Fempharma Europe, LLC, Budapest (HU)

( * ) Notice: Subject to any disclaimer, the term of this patent is extended or adjusted under 35 U.S.C. 154(b) by 1015 days.

(21) Appl. No.: 17/283,241

(22) PCT Filed: Oct. 4, 2019

(86) PCT No.: PCT/IB2019/001065
§ 371 (c)(1),
(2) Date: Apr. 6, 2021

(87) PCT Pub. No.: WO2020/074952
PCT Pub. Date: Apr. 16, 2020

(65) Prior Publication Data
US 2021/0346427 A1     Nov. 11, 2021

Related U.S. Application Data

(60) Provisional application No. 62/742,404, filed on Oct. 7, 2018.

(51) Int. Cl.
| | |
|---|---|
| *A61K 33/30* | (2006.01) |
| *A61K 9/00* | (2006.01) |
| *A61K 31/198* | (2006.01) |
| *A61K 31/202* | (2006.01) |
| *A61K 45/06* | (2006.01) |
| *A61P 15/00* | (2006.01) |
| *A61P 21/00* | (2006.01) |

(52) U.S. Cl.
CPC .......... *A61K 33/30* (2013.01); *A61K 9/0053* (2013.01); *A61K 31/198* (2013.01); *A61K 31/202* (2013.01); *A61K 45/06* (2013.01); *A61P 15/00* (2018.01)

(58) Field of Classification Search
CPC .... A61K 33/30; A61K 9/0053; A61K 31/198; A61K 31/202; A61K 45/06; A61K 2300/00; A61P 15/00; A61P 21/00
See application file for complete search history.

(56) References Cited

U.S. PATENT DOCUMENTS

2008/0031869 A1    2/2008   Fontaine

OTHER PUBLICATIONS

Takacs et al.; "Randomized controlled trial for improved recovery of the pelvic floor after vaginal delivery with a specially formulated postpartum supplement"; Obstet Gynecol Sci 2020;63(3):305-314; published online Apr. 3, 2020.*
Arnouk et al., Physical, Complementary, and Alternative Medicine in the Treatment of Pelvic Floor Disorders, Curr. Urol. Rep. 18:47, 1-13, Jun. 5, 2017.
Pediatric Products Handbook, Mead Johnson Nutrition, 2012, pp. 1-268; https://www.meadjohnson.com/pediatrics/us-en/sites/hcp-usa/files/LB6-complete-5-12.pdf.
Eby, Zinc treatment prevents dysmenorrhea, Medical Hypotheses, Eden Press, Penrith, US; 69(2):297-301, 2007.
Murina et al., Alpha Lipoic Acid Plus Omega-3 Fatty Acids for Vestibulodynia Associated with Painful Bladder Syndrome, J. Obstet. Gynaecol. Can. 39(3):131-137, Feb. 28, 2017.
Takacs, P., Randomized controlled trial for improved recovery of pelvic floor after vaginal delivery witha specifically formulated . . . , FPMRS 25(5 Suppl 1):S90, Sep. 25, 2019.
World Congress on Osteoporosis, Osteoarthritis and Musculoskeletal Diseases, Osteoporos. Int. 27(Suppl 1):S79-S548, May 17, 2016.

* cited by examiner

*Primary Examiner* — Jeffrey T. Palenik
(74) *Attorney, Agent, or Firm* — Grimes & Yvon LLP

(57) ABSTRACT

Provided are a pharmaceutical composition comprising zinc, leucine, and omega-3 fatty acids, formulated for oral delivery; a kit comprising the pharmaceutical composition; and methods of promoting recovery of pelvic floor muscles in a postpartum female subject and of treating pelvic floor dysfunction in a female subject by administering the pharmaceutical composition to the a subject.

15 Claims, 1 Drawing Sheet

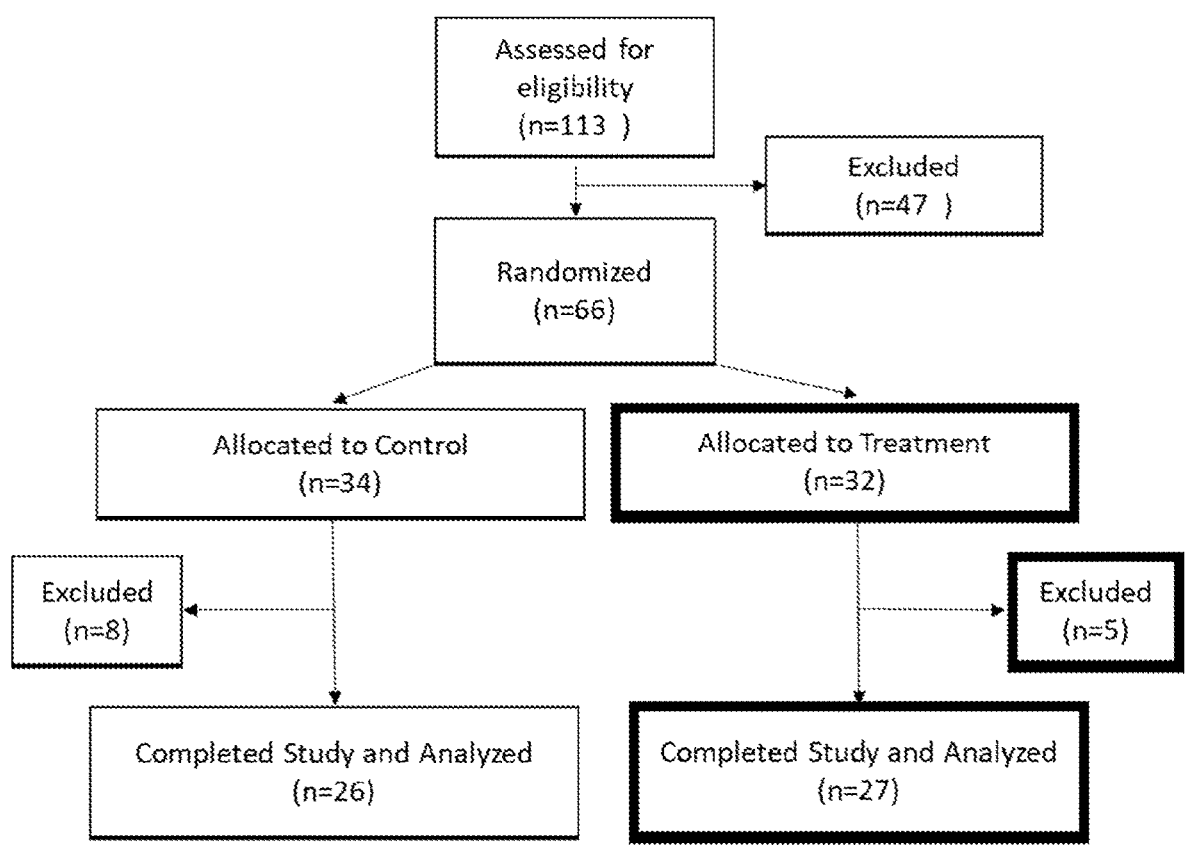

PHARMACEUTICAL COMPOSITION FOR POSTPARTUM RECOVERY AND TREATMENT OF PELVIC FLOOR DYSFUNCTION

CROSS-REFERENCE TO RELATED APPLICATION

This application claims the benefit of priority of U.S. Provisional Patent Application No. 62/742,404, filed on Oct. 7, 2018.

BACKGROUND

Pelvic floor dysfunction is experienced by as many as one third of women, and is characterized by symptoms such as urinary incontinence, fecal incontinence, pelvic organ prolapse, sexual dysfunction, and pelvic pain. There is a clear correlation between urinary incontinence, pelvic floor muscle strength, and the number and type of deliveries.[3,4] Urinary incontinence is not a problem solely for elderly women. Surveys show that 50% of women between 18 and 24 have already experienced unintentional urine loss and 5-72% of the adult female population is affected by this problem.[5] Weakened, damaged pelvic floor muscles can have a negative effect on sexual intercourse as well. These changes affect a woman's general well-being. In addition to childbirth, pelvic floor dysfunction can be caused by obesity, pelvic surgery and/or radiation, traumatic injury or nerve damage in the pelvic region, chronic heavy lifting, or any chronic repetitive stress on the pelvic floor, such as constipation or coughing from COPD.

The pelvis is the lowest part of the abdominal cavity that connects the torso and the lower limbs. The perineum is the connective tissue region between the vagina and the anus. The musculature and connective tissues of the pelvic floor are responsible for maintaining continence of stool and urine as well. The genital hiatus in the front of the pelvic floor is greatly expanded during childbirth to allow the head of the fetus to pass through. After delivery, the stretched musculus levator ani is contracted back to its near original shape and the pelvic floor structure is restored. If the pelvic floor is injured at birth, organs in the pelvis may prolapse; bladder or rectum prolapse and several pelvic floor dysfunctions may anise.

The levator ani muscle plays a prominent role in supporting the pelvis. Levator ani muscles (musculus pubovaginal, puboperineal, pubovisceralis) are connected to the pelvic organs, such as the vagina, which is an 8-12 cm long canal. The vagina is attached to the surrounding levator muscle, supporting the urinary bladder and the urethra from the front, and the rectum at its back wall. Where the vagina is not properly linked to the surrounding muscle and connective tissue ribbons, it cannot provide its supporting function. If the organs supported by the vagina lose their position due to load/pressure and elongation of the connective tissue, it may result in prolapse. Prolapse can happen with the vagina, the bladder, the urethra, the uterus, and/or the rectum. Weakness of the sphincter muscles of the anus may also occur, leading to fecal incontinence or other defecatory dysfunctions.

The most common risk factor among women suffering from these symptoms is the weakness of the pelvic floor muscles. The control of perineum muscles is in strong nexus with the central functions of physical and mental health. Strengthening the muscles of the pelvic floor and perineum after delivery is of critical importance. The appearance of many unpleasant symptoms could be prevented in this way and the original condition could be largely restored. However, postpartum regeneration should be started immediately after delivery. The present invention promotes this regeneration.

Pelvic floor muscle injury commonly occurs during vaginal delivery. The sustained muscle injury leads to a significantly increased risk of the development of pelvic floor dysfunctions, including urinary incontinence, fecal incontinence, pelvic organ prolapse, and sexual dysfunction. Currently, no preventative measure is known to significantly decrease the rate of pelvic floor muscle injury during labor. In addition, no treatment is currently known to help to repair damaged pelvic muscles. Accordingly, there is a need in the art for novel compositions and methods of treating and preventing pelvic floor muscle injury and its resulting conditions.

SUMMARY OF THE INVENTION

Some of the main aspects of the present invention are summarized below. Additional aspects are described in the Detailed Description of the Invention, Examples, Drawings, and Claims sections of this disclosure. The description in each section of this disclosure is intended to be read in conjunction with the other sections. Furthermore, the various embodiments described in each section of this disclosure can be combined in various different ways, and all combinations of disclosed embodiments are intended to fall within the scope of the present invention.

During vaginal delivery it is quite common that the pelvic floor muscles are damaged to some extent; 15-50% of women may be affected.[6-8] If this condition is not properly regenerated and persists for a long period of time, it has a great chance to lead to pelvic floor dysfunctions, including urinary incontinence, fecal incontinence, pelvic organs prolapse, and/or sexual dysfunction. Prior to the present invention, there existed no preventive method that would significantly reduce the pelvic floor muscle injury during pregnancy and childbirth, nor was there any known nutritional supplement or medication that could aid in the recovery of damaged pelvic muscles or improve their function. The present invention promotes the recovery and regeneration of pelvic muscles with utmost efficiency after vaginal birth or other pelvic floor muscle damage. This is the first report demonstrating that a specially formulated dietary supplement improves the recovery of pelvic floor function after pelvic floor muscle injury.

In particular, the herein described study examined the musculature of the pelvic floor and the perineum of women who underwent vaginal delivery, more specifically the regeneration of these muscles by the 6$^{th}$ week after delivery. Mothers participating in the clinical trial were administered a composition of the invention, which composition helped to improve the recovery of over-exerted, loose, or even injured muscles of the pelvic floor and perineum, and can prevent or reduce the occurrence of symptoms of pelvic floor muscle weakness and related symptoms and conditions, such as incontinence or prolapse of female pelvic organs.

In one aspect, the invention provides a pharmaceutical composition comprising zinc, leucine, and omega-3 fatty acids, wherein the supplement is formulated for oral delivery. In a certain embodiment, the supplement further comprises a prenatal vitamin.

In some embodiments, the pharmaceutical composition can comprise about 10 mg to about 40 mg of zinc. In some embodiments, the pharmaceutical composition can comprise about 2 g to about 10 g leucine. In some embodiments, the pharmaceutical composition can comprise about 500 mg to about 1,500 mg omega-3 fatty acids. In certain embodiments, the pharmaceutical composition comprises about 200 mg to about 750 mg DHA. In certain embodiments, the pharmaceutical composition comprises about 200 mg to about 750 mg EPA. In certain embodiments, the pharmaceutical composition comprises about 250 mg to about 500 mg DHA and about 340 mg to about 590 mg EPA. In a particular embodiment, the omega-3 fatty acids are selected from docosahexaenoic acid (DHA), eicosapentaenoic acid (EPA), and a combination of DHA and EPA.

In one embodiment, the pharmaceutical composition comprises about 4 g leucine, about 465 mg EPA, about 375 mg DHA, and a total of about 30 mg zinc.

Also provided is a kit comprising a pharmaceutical composition of the invention, optionally comprising instructions for administration of the pharmaceutical composition.

The pharmaceutical composition of the invention can be for use in promoting recovery of pelvic floor muscles in a postpartum female subject. The pharmaceutical composition of the invention can be for use in treating pelvic floor dysfunction in a female subject.

The invention provides a method of promoting recovery of pelvic floor muscles in a postpartum female subject, the method comprising administering to the subject the pharmaceutical composition of the invention, wherein administration commences within about 48 hours of vaginal delivery by the subject and continues daily for at least about four weeks, at least about five weeks, or at least about six weeks.

In one aspect, the recovery comprises reduced instance of weak vaginal squeeze pressure in the subject, compared with the mean vaginal squeeze pressure of a control population of subjects. In another aspect, the recovery comprises reduced levator-urethra gap (LUG) in the subject, compared with the mean LUG of a control population of subjects. In an additional aspect, the recovery comprises reduced levator hiatus, compared with the mean levator hiatus of a control population of subjects. In a further aspect, the recovery comprises an improvement in Pelvic Organ Prolapse Distress Inventory-6 (POPDI-6) standardized scale score of the subject, compared with a baseline POPDI-6 standardized scale score of the subject.

In an additional embodiment, the invention provides a method of treating pelvic floor dysfunction in a female subject the method comprising administering to the subject the pharmaceutical composition of the invention daily for at least about four weeks, at least about five weeks, or at least about six weeks. In one embodiment, the subject has suffered a traumatic pelvic injury. In one embodiment, the subject has undergone pelvic surgery. In one embodiment, the subject has undergone radiation treatment in her pelvic region. In one embodiment, the subject has suffered nerve damage in her pelvic region. In one embodiment, the subject is obese. In one embodiment, the pelvic floor dysfunction is caused by chronic repetitive stress on the pelvic floor.

BRIEF DESCRIPTION OF THE DRAWING

FIG. 1 shows the flow of participants through a randomized clinical trial. Participants were allocated to treatment or control group.

DETAILED DESCRIPTION OF THE INVENTION

Unless defined otherwise, all technical and scientific terms used herein have the same meaning as commonly understood by one of ordinary skill in the art to which this invention is related.

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Units, prefixes, and symbols are denoted in their Système International de Unites (SI) accepted form. Numeric ranges are inclusive of the numbers defining the range. Where a numeric term is preceded by "about," the term includes the stated number and values ±10% of the stated number. The headings provided herein are not limitations of the various aspects or embodiments of the invention, which can be had by reference to the specification as a whole. Accordingly, the terms defined immediately below are more fully defined by reference to the specification in its entirety.

Wherever embodiments are described with the language "comprising," otherwise analogous embodiments described in terms of "consisting of" and/or "consisting essentially of" are included.

In the postpartum period, the muscle trauma of labor and delivery spontaneously heals in most cases, but often, mothers experience moderate prolapse or stress incontinence. The present invention shows that daily supplementation with a specially formulated pharmaceutical composition that helps postpartum women recover from delivery-induced pelvic floor muscle injuries and related symptoms/conditions. In particular, postpartum women receiving a specially formulated postpartum recovery supplement had improved recovery of pelvic floor function after vaginal delivery at 6 weeks after delivery. Women randomized to the treatment group taking the daily supplement were less likely to have weak vaginal squeeze pressure, presence of levator muscle injury, less anterior vaginal prolapse at or beyond the hymenal ring or bothersome bulge symptoms, and less likely to have wide genital hiatus, compared to women receiving prenatal vitamins only at 6 weeks after vaginal delivery.

The nutritional supplement of the invention contains ingredients that promote the restoration of muscular injuries in 6 weeks following birth and can be taken during lactation. In certain embodiments, the pharmaceutical composition comprises a prenatal vitamin. Any prescription or over-the-counter prenatal multivitamin is suitable. Typically, prenatal vitamins contain more folic acid and iron than standard multivitamins.

Zinc is the second most common trace element in the human body. It is the cofactor of countless enzymes, and it is present in nearly 10% of human proteins as structural, catalytic, or signal mediator.[9-13] Zinc is a component of several metalloenzymes, and plays a very important role in wound healing, connective tissue biosynthesis, and homeostasis. It also plays an important role in collagen metabolism, and is an indispensable cofactor of matrix metalloproteases (MMP) and procollagen C-proteases. Previous studies indicated that in human vaginal smooth muscle cells, zinc at a tissue level of 20 µM has a beneficial effect on the production of extracellular components produced by the muscle cells, thereby increasing the amount of collagen and elastin production and the amount of smooth muscle.

Zinc serum levels have been shown to decrease significantly after vaginal delivery, but not after elective cesarean sections.[19] By oral zinc supplementation, the present invention achieves a saturated zinc level in vaginal tissue; therefore, zinc is available in an optimal amount for being a co-factor for the enzymes involved in tissue regeneration. Since zinc supplementation lasts only up to about 6 weeks, the maximum recommended quantity is administered to subjects. It is possible to achieve zinc saturation in the body by the addition of 20-30 mg Zn per day. This daily dose can be safely taken and expected that the vaginal tissue zinc level will be about 20 µM.

In some embodiments, the pharmaceutical composition of the invention comprises a total of about 5-40 mg, at least about 5, 10, 15, 20, 25, 30, 35, or 40 mg of zinc, or any dosage range of zinc having these amounts as endpoints. In embodiments where the pharmaceutical composition comprises a prenatal vitamin, the total amount of zinc in the pharmaceutical composition includes any dose of zinc in the prenatal vitamin, along with any additional dose, exclusive of that in the prenatal vitamin.

In humans, it has been shown that omega-3 fatty acids are able to increase the production of muscle proteins, thereby enhancing muscle strength.[22-25] Such experiments have not been carried out in women recovering from delivery, so prior to the present study it was unknown whether omega-3 fatty acid supplementation would have a beneficial effect on muscle recovery in postpartum women. Omega-3 fatty acids are beneficial in pregnancy and can be safely taken by lactating postpartum women.[26]

Omega-3 fatty acids include docosahexaenoic acid (DHA), eicosapentaenoic acid (EPA), and u-linolenic acid (ALA). The pharmaceutical composition of the invention can comprise any one or more of DHA, EPA, and ALA. The pharmaceutical composition preferably comprises DHA, EPA, or a combination of DHA and EPA. The daily dosage of omega-3 fatty acids is preferably about 500 mg to about 1,500 mg. The pharmaceutical composition can comprise at least about 200, 225, 250, 275, 300, 325, 350, 375, 400, 425, 450, 475, 500, 525, 550, 575, 600, 625, 650, 675, 700, 725, or 750 mg DHA, or any dosage range of DHA having these amounts as endpoints. The pharmaceutical composition can comprise at least about 200, 225, 250, 275, 300, 325, 350, 375, 400, 425, 450, 475, 500, 525, 550, 575, 600, 625, 650, 675, 700, 725, or 750 mg EPA, or any dosage range of EPA having these amounts as endpoints. In one preferred embodiment, the omega-3 fatty acids are administered in a ratio of about 465 mg EPA and about 375 mg DHA. In embodiments where the pharmaceutical composition comprises a prenatal vitamin, the total amount of omega-3 fatty acids in the pharmaceutical composition includes any dose of omega-3 fatty acids in the prenatal vitamin, along with any additional dose, exclusive of that in the prenatal vitamin.

Leucine is an essential amino acid, and is the only nutritional amino acid capable of stimulating the synthesis of muscle proteins. It enhances regeneration and prevents muscle tissue degradation. Leucine can also prevent muscular weakness related to aging.[27] However, the role of leucine in muscle recovery after injury has not been proven previously. The pharmaceutical composition of the invention can comprise, for example, about 2-10 g leucine, at least about 2, 2.5, 3, 3.5, 4, 4.5, 5, 5.5, 6, 6.5, 7, 7.5, 8, 8.5, 9, 9.5, or 10 g leucine, or any dosage range of leucine having these amounts as endpoints. In embodiments where the pharmaceutical composition comprises a prenatal vitamin, the total amount of leucine in the pharmaceutical composition includes any dose of leucine in the prenatal vitamin, along with any additional dose, exclusive of that in the prenatal vitamin.

By "subject" or "individual" or "patient" is meant a mammalian subject, for whom diagnosis, prognosis, or therapy is desired. Mammalian subjects include humans, domestic animals, farm animals, sports animals, and zoo animals including, e.g., humans, non-human primates, dogs, cats, guinea pigs, rabbits, rats, mice, horses, cattle, and so on.

The subject may suffer from pelvic floor dysfunction. Pelvic floor dysfunction is characterized by symptoms that include, for example, urinary incontinence, fecal incontinence, pain or pressure in the pelvic region, discomfort during sexual intercourse, and muscle spasms in the pelvis. In some embodiments, the subject may have undergone childbirth, particularly vaginal childbirth. In some embodiments, the subject may have sustained a traumatic injury to the pelvis, may have undergone pelvic surgery, and/or may have sustained nerve damage in the pelvis. In some embodiments, the subject is obese. In some embodiments, pelvic floor dysfunction is the result of injury due to chronic repetitive stress on the pelvic floor. Chronic repetitive stress can be caused, for example, by chronic heavy lifting, by constipation, or by chronic coughing, such as from chronic obstructive pulmonary disease (COPD).

Weak vaginal squeeze pressure has been associated with more anterior compartment prolapse and with minor and major avulsion.[37] Assessment of pelvic floor strength during gynecological examination may help to identify women with fascial defects of the pelvic floor, as well as those at risk of genital prolapse or urinary incontinence. Pelvic floor muscle function can be assessed in a variety of ways. For example, vaginal squeeze pressure has been used as a marker for pelvic floor function.[39] Levator injury has been associated with weaker pelvic floor muscle contraction measured with palpation, perineometry, and by ultrasound.[40] Magnetic resonance imaging (MRI) and measurement using a dynamometer are other methods of assessing pelvic floor muscle function. A perineometer or vaginal manometer is a very effective and precise instrument for measuring the strength of voluntary contractions of the pelvic floor muscles. The hand-held clinical biofeedback perineometer is controlled by a microprocessor. Pelvic floor contraction causes air pressure in the sensor to be transferred through the connecting tube and displayed on the readout unit.

A "control population" is a group of subjects that have not received treatment. For purposes of the present disclosure, subjects in the control population are at approximately the same period postpartum as the subject being compared to the control population. For example, when comparing the vaginal squeeze pressure of a subject receiving the pharmaceutical composition of the invention for four weeks postpartum, that subject's vaginal squeeze pressure is compared with the average vaginal squeeze pressure of subjects at about four weeks postpartum who did not receive the pharmaceutical composition of the invention.

"Postpartum" refers to the period immediately following childbirth through about six months following childbirth.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already with the disorder. In certain embodiments, a subject is successfully "treated" for a disease or disorder according to the methods provided herein if the patient shows, e.g., total, partial, or transient alleviation or elimination of symptoms associated with the disease or disorder; diminishment of the extent of the condition, disease, or disorder; stabilization (i.e., not worsening) of the condition, disease, or disorder; or slowing of progression of the condition, disease or disorder.

"Prevent" or "prevention" refers to prophylactic or preventative measures that prevent and/or slow the development of a targeted pathologic condition or disorder. Thus, those in need of prevention include those at risk of or susceptible to developing the disorder. Subjects that are at risk of or susceptible to developing pelvic floor dysfunction or muscle injury include, but are not limited to, women who give birth, women who are obese, women who have undergone pelvic surgery or radiation treatment in the pelvic area, women who have sustained a traumatic injury and/or nerve damage in the pelvic area. In certain embodiments, a disease or disorder is successfully prevented according to the methods provided herein if the patient develops, transiently or permanently, e.g., fewer or less severe symptoms associated with the disease or disorder, or a later onset of symptoms associated with the disease or disorder, than a patient who has not been subject to the methods of the invention.

An "active agent" is an agent which itself has biological activity, or which is a precursor or prodrug that is converted in the body to an agent having biological activity. In some embodiments, the agents are small molecule compounds, including vitamins, minerals, amino acids, and fatty acids. In other embodiments, the agents are macromolecules, such as polynucleotides (e.g., inhibitory RNA) or polypeptides (e.g., antibodies).

An "effective amount" of a composition as disclosed herein is an amount sufficient to carry out a specifically stated purpose. An "effective amount" can be determined empirically and in a routine manner, in relation to the stated purpose, route of administration, and dosage form.

"Oral delivery" includes, without limitation, oral, sublingual, and buccal delivery.

The term "pharmaceutical composition" refers to a collection of ingredients or substituents in such form as to permit the biological activity of the active ingredient(s) to be effective, and which contains no additional components that are unacceptably toxic to a subject to which the composition would be administered. Pharmaceutical compositions can be in numerous dosage forms or combinations of dosage forms, for example, tablet, capsule, liquid, solution, softgel, suspension, emulsion, syrup, elixir, tincture, film, powder, hydrogel, ointment, paste, cream, lotion, gel, mousse, foam, lacquer, spray, aerosol, inhaler, nebulizer, ophthalmic drops, patch, suppository, and/or enema. In embodiments in which more than one active agent is administered, the agents can be administered together (for example, in the same formulation and/or at the same time), or separately (for example, in different formulations and/or at different times). Accordingly, a pharmaceutical composition of the invention can comprise one or multiple dosage units.

The pharmaceutical composition can be administered according to any suitable dosing regimen, for example, where the daily dose is divided into two or more separate doses. It is within the skill of the ordinary artisan to determine a dosing schedule and duration. In some embodiments, the pharmaceutical composition is administered orally once a day or in a divided dose twice a day. For example, a method of administering a pharmaceutical composition comprising 4 g leucine, 470 mg EPA, 380 mg DHA, and 30 mg zinc daily could include administration of 4 g leucine, 470 mg EPA, 380 mg DHA, and 30 mg zinc one time per day or administration of 2 g leucine, 235 mg EPA, 190 mg DHA, and 15 mg zinc twice per day, etc.

Also within the scope of the invention are kits comprising the pharmaceutical compositions as provided herein and instructions for use. Kits typically include a label indicating the intended use of the contents of the kit. The term "label" includes any writing, or recorded material supplied on or with the kit, or which otherwise accompanies the kit. A kit of the invention can comprise, for example, 7, 14, 21, 28, 35, or 42 daily doses of the pharmaceutical composition of the invention. In some embodiments, the components of each daily dose are packaged together, for example, in a pouch, blister pack, etc. In some embodiments, the components of each daily dose are divided into two packages for administration twice daily.

All of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Documents incorporated by reference into this text are not admitted to be prior art.

Embodiments of the present disclosure can be further defined by reference to the following non-limiting examples. It will be apparent to those skilled in the art that many modifications, both to materials and methods, can be practiced without departing from the scope of the present disclosure.

EXAMPLES

Example 1

Study Design and Enrollment

Primipara women within 48 hours of vaginal delivery following a normal prenatal course without significant medical comorbidities were randomized in a 1:1 ratio to receive daily oral supplementation for 6 weeks with either a combination of regular prenatal vitamin (PNV), leucine 4 gm/day, zinc (adjusted to 30 mg/day) and omega-3 fatty acid 900 mg/day (465 mg EPA and 375 mg DHA) or only PNV daily (control group). Oral supplementation started within 48 hours after delivery. Patients were reminded by weekly phone calls and or text messages to take the supplements. Patients and evaluating physicians were blinded to the allocation. All study subjects were over the age of 18 and signed a document representing their informed consent to participate in research.

Exclusion criteria were prior delivery (vaginal or cesarean section), multiple gestation, preterm delivery (<37 weeks), operative vaginal delivery other than outlet vacuum assisted vaginal delivery, gestational diabetes mellitus, conditions requiring chronic daily medications, history of liver disease, zinc or copper deficiency, fish allergy or other allergy to any component of the supplement, and vegetarian diet. Patients with collagen disease or connective tissue disease were excluded. Active vaginal inflammation or postpartum infection was also an exclusion factor.

FIG. 1 summarizes the assessment for eligibility, randomization, allocation and exclusions of participants. Of the 113 women screened, 66 met entry criteria and were randomized. Thirty-four women were randomly assigned to the control group and thirty-two to the control group. Fifty-three women completed the trial: 26 in the control group and 27 in the treatment group.

At enrollment, demographic and clinical characteristics were prospectively collected (age, gravida, parity, BMI, gestational age, length of second stage, anesthesia, newborn weight and head circumference, lacerations during delivery, episiotomy, breast feeding) and entered into a database. Demographic and baseline characteristics at randomization are presented in Table 1. There were no statistically significant differences in distribution of any of the demographic variables between the control and treatment groups. Most women underwent an uncomplicated vaginal delivery but three who underwent an outlet vacuum assisted vaginal delivery all in the treatment group. The majority of women did have mediolateral episiotomy at delivery. Birthweight and fetal head circumference were similar between the control and treatment group.

TABLE 1

Demographic and Clinical Characteristics of Participants

|  | Control (n = 26) | Treatment (n = 27) | P-value |
| --- | --- | --- | --- |
| Age (years, mean ± SD) | 28 ± 3 | 29 ± 3 | 0.07 |
| Gravida (median, range) | 1 (1-3) | 1 (1-3) | 1 |
| Pre-pregnancy BMI (kg/m$^2$, mean ± SD) | 21.7 ± 4.6 | 21.9 ± 3.8 | 0.83 |
| BMI at Delivery (kg/m$^2$, mean ± SD) | 28.3 ± 4.3 | 26.9 ± 3.3 | 0.44 |
| Estimated Gestational Age (weeks, mean ± SD) | 38.6 ± 1.4 | 38.7 ± 1.4 | 0.89 |
| Birthweight (grams, mean ± SD) | 3307 ± 401 | 3411 ± 111 | 0.36 |
| Head circumference (cm, mean ± SD) | 33 ± 1 | 33 ± 1 | 0.93 |
| Length of second stage (minutes, mean ± SD) | 27 ± 11 | 32 ± 13 | 0.17 |
| Episiotomy (n, %) | 25 (96) | 25 (92) | 1 |
| Epidural (n, %) | 18 (69) | 16 (60) | 0.56 |
| Vacuum extraction (n, %) | 0 (0) | 3 (11) | 0.23 |
| Breastfeeding (n, %) | 26 (100) | 27 (100) | 1 |

After six weeks, participants returned for blood collection and a general gynecological examination. Patients completed a standard questionnaire for assessing postnatal status and were asked about compliance with the daily supplement and when the last dose of supplement was taken. Muscle regeneration rate was measured in the two study groups by measuring the strength of voluntary contractions of the vagina using a perineometer (Peritron, Laborie, USA). The state of the pelvic floor musculature was assessed with a gynecological transperineal ultrasound. The levator urethra gap (LUG) and levator hiatus (LH) were determined as described previously by a GE Voluson S8 3D ultrasound equipment (GE Medical Systems, USA).[30-32] Both LUG and LH give a very accurate picture of the pelvic muscle's condition.

The above measurements were performed only at 6 weeks after birth for several reasons. Perineometric measurements performed directly before delivery do not provide reproducible results, since the vagina and the pelvis are significantly changed that time and muscles are often edematous. There is increased abdominal pressure and the Valsalva maneuver may not be reproduced well. Furthermore, the examination may be uncomfortable for pregnant women. In addition, transperineal ultrasound measurements are not completely reliable before birth because the muscle may have a significant edema causing inaccuracies in the measurements.

Serum Zinc Levels

Serum levels of zinc were measured at baseline and 6 weeks postpartum and used as a marker of compliance. Serum zinc level determination was carried out by inductively coupled plasma optical emission spectrometry (ICP-OES 5100, Agilent Technologies). The measurements were conducted in SVDV (Synchronous Vertical Dual View) mode, gaining intensity data from axial and radial view, simultaneously. Automatic sample introduction was applied (SPS 4, Agilent Technologies) and the samples were measured in a completely randomized design.

Zinc levels and other trace element levels were measured to trace the change in blood zinc and other trace element concentration directly after delivery and after the regeneration time. Serum zinc concentration was used to assess the overall zinc homeostasis. Communications published in the literature suggest that serum zinc level is the best approach to tissue zinc level. Vaginal biopsy could be an alternative method for assessing tissue zinc level. It was expected that zinc levels should rise both in the treatment and control groups compared to the baseline values obtained within 48 hours after delivery, since both the control and treatment group received daily zinc supplementation (15 mg vs. 30 mg, respectively).

Consistent with the patient-reported compliance in both groups, the mean zinc levels increased significantly from baseline compared to 6 weeks after delivery (Table 2). The mean zinc level was 10% higher in the treatment group at 6 weeks postpartum compared to the control group. Average zinc levels on increased significantly more in the treatment group from baseline to 6 weeks postpartum compared to the control group (mean±SD A zinc level increase 0.48±0.24 vs. 0.29±0.20, P<0.01).

TABLE 2

Serum Zinc and Copper Levels

|  | Control (n = 26) | Treatment (n = 27) | P-value |
| --- | --- | --- | --- |
| Zinc level after delivery (mg/l, mean ± SD) | 0.71 ± 0.19 | 0.62 ± 0.10 | 0.08 |
| Zinc level 6 weeks postpartum (mg/l, mean ± SD) | 1.00 ± 0.19 | 1.10 ± 0.25 | 0.13 |
| P-value | <0.01 | <0.01 |  |

Primary Outcomes

Co-Primary outcomes were (1) vaginal squeeze pressure measured by the Peritron perineometer[33,34] and (2) levator muscle injury diagnosed by large (≥25 mm) levator-urethra gap (LUG) measured by transperineal 3D tomographic ultrasound,[30-32,35] both assessed at 6 weeks postpartum. The results obtained by the perineometer are described in Table 3. Weak pelvic floor muscle strength (defined as the mean of three vaginal squeeze pressure measurements by the perineometer ≤17 cmH$_2$O) was significantly less frequent in the treatment group compared to the control group at 6 weeks after delivery (28% vs. 58%, P=0.03). The risk of having a weak vaginal squeeze pressure was reduced by 52% in the treatment group compared to the control group at 6 weeks postpartum [Risk Ratio=0.48, 95%; Confidence Intervals (0.23-0.98), P=0.03].

TABLE 3

Measurement of Vaginal Squeeze Pressure

| | Control (n = 26) | Treatment (n = 27) | P-value |
|---|---|---|---|
| Vaginal squeeze pressure (cmH$_2$O, mean ± SD) | 21 ± 17 | 22 ± 13 | 0.83 |
| Oxford scale (median, range) | 3 (1-5) | 3 (1-4) | 0.68 |

The likelihood of major levator trauma associated with vaginal delivery increases significantly from 15% at age 20 to over 50% at age 40.[6] Pelvic floor muscle injury has been linked to anterior and central compartment prolapse, and likely represents the missing link between delivery and the development of prolapse. A levator avulsion seems to increase the risk of significant anterior and central compartment prolapse by three fold.[38] Women with persistent levator avulsion have significantly worse deterioration patterns of muscle strength, hiatus measurements, and vaginal symptoms (loose vagina/lump sensation).[36,37] These findings emphasizes the importance of proper recovery from pelvic floor muscle injuries sustained at delivery.

In the present study, both right and left sided LUG were significantly larger in the control group compared to the treatment group (Table 4). Large LUG (≥25 mm) is a good indicator of a levator muscle injury, mainly avulsion. Unilateral levator injury was defined by LUG≥25 mm on at least one side. Unilateral levator avulsion was significantly less frequent in the treatment group compared to the control group at 6 weeks after delivery (3.7% vs. 34.6%, P<0.01). The presence of unilateral levator avulsion was reduced by almost 90% in the treatment group compared to the control group at 6 weeks postpartum [Risk Ratio=0.10, 95%; Confidence Intervals (0.01-0.78)].

Bilateral avulsion was defined by LUG≥25 mm on both sides. Similar to unilateral avulsion, bilateral levator avulsion was significantly less frequent in the treatment group compared to the control group at 6 weeks after delivery (3.7% vs. 38.4%, P<0.01). The presence of bilateral levator avulsion was reduced by 90% in the treatment group compared to the control group at 6 weeks postpartum [Risk Ratio=0.09, 95%; Confidence Intervals (0.01-0.70), P<0.01]. In addition, the levator hiatus was significantly smaller in the treatment group compared to the control group at 6 weeks after delivery (15.5±2.4 vs. 17.7±2.7, P<0.01).

TABLE 4

Levator-Urethra Gap and Levator Hiatus

| | Control (n = 26) | Treatment (n = 27) | P-value |
|---|---|---|---|
| Right sided LUG (mm, mean ± SD) | 24.9 ± 4.2 | 21.1 ± 2.9 | <0.01 |
| Left sided LUG (mm, mean ± SD) | 24.9 ± 3.7 | 20.1 ± 2.8 | <0.01 |
| Levator Hiatus (cm$^2$, mean ± SD) | 17.7 ± 2.7 | 15.5 ± 2.4 | <0.01 |

Secondary Outcomes

Secondary outcomes were (1) Pelvic Organ Prolapse Quantification (POP-Q) measured at 6 weeks postpartum; (2) validated Pelvic Organ Prolapse Distress Inventory-6 (POPDI-6) and Urinary Distress Inventory-6 (UDI-6) Questionnaires at enrollment (baseline) and at 6 weeks postpartum; and (3) digital assessment of the pelvic muscle strength by Oxford Scale measured at 6 weeks postpartum.

The results of the POP-Q measurement are shown in Table 5. There were no significant differences between the mean POP-Q measurement between the control and treatment group. However, anterior vaginal wall prolapse at or beyond the hymenal ring was significantly more common in the control group compared to the treatment group (19% vs. 0%, P=0.02). This could be very well explained by the fact that the control group displayed significantly larger LUG, an indicator that more levator avulsion causes the presence of more anterior vaginal wall prolapse. Also, wide genital hiatus (defined as GH≥4 cm) was significantly more frequent in the control group compared to the treatment group at 6 weeks after delivery (46% vs. 18%, P=0.01), also likely the result of the presence of levator injuries. The risk of wide genital hiatus was almost 3 times higher in the control group compared to the treatment group [Risk Ratio=2.95, 95%; Confidence Interval (1.19-7.30), P-value=0.01].

TABLE 5

Pelvic Organ Prolapse Quantification (POP-Q)

| Anatomical Position | Control (n = 26) | Treatment (n = 27) | P-value |
|---|---|---|---|
| Aa | -1.4 ± 1.0 | -1.63 ± 0.8 | 0.41 |
| Ba | -1.4 ± 1.0 | -1.63 ± 0.8 | 0.61 |
| C | -6.0 ± 0.8 | -6.2 ± 0.9 | 0.34 |
| GH | 3.56 ± 0.7 | 3.40 ± 0.7 | 0.45 |
| PB | 2.67 ± 0.5 | 2.56 ± 0.4 | 0.41 |
| TVL | 8.8 ± 0.7 | 8.8 ± 0.8 | 0.85 |
| Ap | -1.73 ± 0.9 | -1.70 ± 0.9 | 0.87 |
| Bp | -1.73 ± 0.9 | -1.70 ± 0.9 | 0.90 |
| D | -7.5 ± 3.2 | -7.8 ± 0.94 | 0.61 |

Aa: position of the anterior vaginal wall 3 cm proximal to the hymen; Ba: most distal position of the remaining upper anterior vaginal wall; C: position of the cervix; D: position of the cul-de-sac; Ap: position of the posterior vaginal wall 3 cm proximal to the hymen; Bp: most distal position of the remaining upper posterior vaginal wall; GH: genital hiatus; TVL: total vaginal length; PB: perineal body.

The mean POPDI-6 and UDI-6 standardized scale scores were similar between the treatment and control groups, but significantly more women reported bothersome bulge symptoms (Q #3 on POPDI-6) from the control group compared to the treatment group at 6 weeks postpartum (19% vs. 0%, P=0.02). Also, the mean standardized POPDI-6 score significantly improved in the treatment group by 6 weeks compared to the baseline score (4.6±6.3 vs. 1.7±3.9, P=0.02), but did not improve significantly in the control group (6.6±13.0 vs. 2.2±3.5, P=0.11). The mean standardized UDI-6 score significantly improved in both the control and the treatment groups by 6 weeks compared to the baseline score [18.4±16.8 vs. 3.8±5.5, P<0.01 (control) and 22.3±14.5 vs. 5.4±9.7, P<0.01 (treatment group)].

TABLE 6

Validated POPD-6 and UDI-6 Questionnaire Results

| | Control (n = 26) | Treatment (n = 27) | P-value |
|---|---|---|---|
| Baseline POPDI-6 (mean ± SD) | 6.6 ± 13.0 | 4.6 ± 6.3 | 0.46 |
| Baseline UDI-6 (mean ± SD) | 18.4 ± 16.8 | 22.3 ± 14.5 | 0.37 |
| POPDI-6 at 6 weeks (mean ± SD) | 2.2 ± 3.5 | 1.7± 3.9 | 0.60 |
| UDI-6 at 6 weeks (mean ± SD) | 3.8 ± 5.5 | 5.4 ± 9.7 | 0.48 |

Data provided as standardized scale scores.

SigmaStat/SPSS software was used for statistical calculations. Descriptive statistics were calculated for all variables of interest. Means and standard deviations were calculated for continuous outcomes. Frequency and percentage were calculated for categorical outcomes. Student t-test was used to compare the mean values between two groups. Paired t-test was used to compare paired data which was obtained at baseline and at 6 weeks (zinc levels, questionnaires). Frequencies were analyzed by Fisher exact test. The study has adequate power to detect a difference after 46 patients' enrollment. Power analysis was performed based on a pilot study, which revealed that weak pelvic floor muscle is ≤17 cmH$_2$O as measured by our perineometer. To have a power of 80% and a significance level of 5% to detect a 40% difference in the rate of weak vaginal squeeze pressure, a sample size of 46 was needed with 23 patients in each arm of our RCT. Statistical significance was defined as a P-value <0.05 using two-tailed tests.

This study indicates that the specially formulated pharmaceutical composition of the invention containing zinc, leucine, and omega-3 fatty acids in a unique ratio contributed to the faster and better recovery of the pelvic floor. The pelvic floor is a very complex system of muscles and connective tissues required to function in perfect harmony to provide the necessary support for the pelvic organs (bladder, rectum, internal female organs, and the vagina). During pregnancy, delivery and postpartum period the pelvic floor undergoes tremendous amount of remodeling. Our postpartum recovery supplement helped to direct the natural healing process of the pelvic floor to recover faster and restore its function by 6 weeks compared to a traditional prenatal vitamin.

This study is the first trial testing the effects of a food supplement on the recovery of the postpartum pelvic floor function. Important strengths of the study are its randomized and double-blinded nature; both participants and investigators performing the perinoemetry, the transperineal ultrasound, and pelvic floor assessment were blinded to the allocation. In addition, the LUG measurements were performed prior to breaking the randomization. Another strength of this study was the participants' high compliance with taking the supplements, as reflected by the significant elevation of the zinc serum levels in both the treatment and control groups. Previous research has revealed that after vaginal delivery the zinc levels are expected to decrease significantly,[19] but in the present study, population zinc levels increased significantly, suggesting compliance with the allocated supplements.

In summary, patients receiving the specially formulated postpartum recovery supplement had improved recovery of the pelvic floor function after vaginal delivery. Postpartum women receiving the supplement were less likely to have weak vaginal squeeze pressure, presence of levator muscle injury, less anterior vaginal prolapse at or beyond the hymenal ring or bothersome bulge symptoms, and less likely to have wide genital hiatus compared to women receiving prenatal vitamins only at 6 weeks after vaginal delivery.

Exemplary Embodiments

The following paragraphs provide non-limiting examples of embodiments of the invention.

A pharmaceutical composition comprising zinc, leucine, and omega-3 fatty acids, wherein the composition is formulated for oral delivery.

The pharmaceutical composition of the preceding paragraph, further comprising a prenatal vitamin.

The pharmaceutical composition of any preceding paragraph, wherein the omega-3 fatty acids are selected from docosahexaenoic acid (DHA), eicosapentaenoic acid (EPA), and a combination of DHA and EPA.

The pharmaceutical composition of any preceding paragraph, comprising a total of about 10 mg to about 40 mg zinc.

The pharmaceutical composition of any preceding paragraph, comprising a total of about 2 g to about 10 g leucine.

The pharmaceutical composition of any preceding paragraph, comprising a total of about 500 mg to about 1,500 mg omega-3 fatty acids.

The pharmaceutical composition of any preceding paragraph, comprising about 200 mg to about 750 mg DHA.

The pharmaceutical composition of any preceding paragraph, comprising about 200 mg to about 750 mg EPA.

The pharmaceutical composition of any preceding paragraph, comprising about 250 mg to about 500 mg DHA and about 340 mg to about 590 mg EPA.

The pharmaceutical composition of any preceding paragraph, comprising about 4 g leucine, about 465 mg EPA, about 375 mg DHA, and a total of about 30 mg zinc.

A kit comprising the pharmaceutical composition of any preceding paragraph.

The kit of the preceding paragraph, further comprising instructions for administration.

The pharmaceutical composition or kit of any preceding paragraph for use in promoting recovery of pelvic floor muscles in a female subject.

The pharmaceutical composition or kit of any preceding paragraph for use in treating pelvic floor dysfunction in a female subject.

A method of promoting recovery of pelvic floor muscles in a postpartum female subject, the method comprising administering to the subject the pharmaceutical composition of any preceding paragraph, wherein administration commences within about 48 hours of vaginal delivery by the subject and continues daily for at least about four weeks.

The method of the preceding paragraph, wherein administration continues daily for at least about five weeks.

The method of any preceding paragraph, wherein administration continues daily for at least about six weeks.

The method of any preceding paragraph, wherein the recovery comprises reduced instance of weak vaginal squeeze pressure in the subject, compared with the mean vaginal squeeze pressure of a control population of subjects.

The method of any preceding paragraph, wherein the recovery comprises reduced levator-urethra gap (LUG) in the subject, compared with the mean LUG of a control population of subjects.

The method of any preceding paragraph, wherein the recovery comprises reduced levator hiatus, compared with the mean levator hiatus of a control population of subjects.

The method of any preceding paragraph, wherein the recovery comprises an improvement in Pelvic Organ Prolapse Distress Inventory-6 (POPDI-6) standardized scale score of the subject, compared with a baseline POPDI-6 standardized scale score of the subject.

A method of treating pelvic floor dysfunction in a female subject the method comprising administering to the subject the pharmaceutical composition of any preceding paragraph daily for at least about four weeks.

The method of the preceding paragraph, comprising daily administration for at least about five weeks.

The method of any preceding paragraph, comprising daily administration for at least about six weeks.

The method of any preceding paragraph, wherein the subject has suffered a traumatic pelvic injury.

The method of any preceding paragraph, wherein the subject has undergone pelvic surgery.

The method of any preceding paragraph, wherein the subject has undergone radiation treatment in her pelvic region.

The method of any preceding paragraph, wherein the subject has suffered nerve damage in her pelvic region.

The method of any preceding paragraph, wherein the subject is obese.

The method of any preceding paragraph, wherein the pelvic floor dysfunction is caused by chronic repetitive stress on the pelvic floor.

REFERENCES

1. Rortveit G, Hannestad Y S. Association between mode of delivery and pelvic floor dysfunction. *Tidsskr Nor Laegeforen*. 2014; 134(19):1848-1852.
2. Chaliha C. Postpartum pelvic floor trauma. *Curr Opin Obstet Gynecol*. 2009; 21(6):474-479.
3. Ozdemir O, Bakar Y, Ozengm N, Duran B. The effect of parity on pelvic floor muscle strength and quality of life in women with urinary incontinence: a cross sectional study. *J Phys Ther Sci*. 2015; 27(7):2133-2137.
4. Hilde G, Stor-Jensen J, Siafarikas F, Engh M E, Brokken I H, Bo K. Impact of childbirth and mode of delivery on vaginal resting pressure and on pelvic floor muscle strength and endurance. *Am J Obstet Gynecol*. 2013; 208(1):50.e51-57.
5. Aoki Y, Brown H W, Brubaker L, Comu J N, Daly J O, Cartwright R. Urinary incontinence in women. *Nat Rev Dis Primers*. 2017; 3:17097.
6. Dietz H P, Simpson J M. Does delayed child-bearing increase the risk of levator injury in labour? *Aust N Z J Obstet Gynaecol*. 2007; 47(6):491-495.
7. Dietz H P. Ultrasound in the assessment of pelvic organ prolapse. *Best Pract Res Clin Obstet Gynaecol*. 2018.
8. Atan I K, Lin S, Dietz H P, Herbison P, Wilson P D, Group P S. Levator Avulsion Is Associated With Pelvic Organ Prolapse 23 Years After the First Childbirth. *J Ultrasound Med*. 2018.
9. NIH Zinc fact sheet (National Institute of Health Office of Dietary Supplements: available at: ods.od.nih.gov/factsheets/Zinc-HealthProfessional/.
10. Maret W, Sandstead H H. Zinc requirements and the risks and benefits of zinc supplementation. *J Trace Elem Med Biol*. 2006; 20(1):3-18.
11. Kambe T, Tsuji T, Hashimoto A, Itsumura N. The Physiological, Biochemical, and Molecular Roles of Zinc Transporters in Zinc Homeostasis and Metabolism. *Physiol Rev*. 2015; 95(3):749-784.
12. Institute of Medicine, Food and Nutrition Board. Dietary Reference Intakes for Vitamin A, Vitamin K, Arsenic, Boron, Chromium, Copper, Iodine, Iron, Manganese, Molybdenum, Nickel, Silicon, Vanadium, and Zinc external link disclaimer. Washington, DC: National Academy Press, 2001.
13. See ref. 9.
14. Takacs P, Jaramillo S, Zhang Y, et al. The effects of PPARδ agonist and zinc on ovariectomized rats' vagina. *Female Pelvic Med Reconstr Surg*. 2013; 19(3):126-131.
15. Takacs P, Zhang Y, Candiotti K, Jaramillo S, Medina C A. Effects of PPAR-delta agonist and zinc on vaginal smooth muscle cells collagen and tropoelastin production. *Int Urogynecol J* 2012; 23(12):1775-1779.
16. Taneja S K, Kaur R. Pathology of ovary, uterus, vagina and gonadotrophs of female mice fed on Zn-deficient diet. *Indian J Exp Biol*. 1990; 28(11):1058-1065.
17. Kelkar M A, Khar S K, Mandakhot V M. Studies on antepartum prolapse of the vagina in buffalo—plasma trace element concentrations. *Arch Exp Veterinarmed*. 1989; 43(2):315-318.
18. Ozdemir S, Ozis E S, Gulpinar K, et al. The value of copper and zinc levels in hernia formation. *Eur J Clin Invest*. 2011; 41(3):285-290.
19. Schulpis K H, Karakonstantakis T, Vlachos G D, et al. Maternal-neonatal magnesium and zinc serum concentrations after vaginal delivery. *Scand J Clin Lab Invest*. 2010; 70(7):465-469.
20. Lazebnik N, Kuhnert B R, Kuhnert P M, Thompson K L. Zinc status, pregnancy complications, and labor abnormalities. *Am J Obstet Gynecol*. 1988; 158(1):161-166.
21. Caulfield L E, Zavaleta N, Shankar A H, Merialdi M. Potential contribution of maternal zinc supplementation during pregnancy to maternal and child survival. *Am J Clin Nutr*. 1998; 68(2 Suppl):499S-508S.
22. Smith G I, Julliand S, Reeds D N, Sinacore D R, Klein S, Mittendorfer B. Fish oil-derived n-3 PUFA therapy increases muscle mass and function in healthy older adults. *Am J Clin Nutr*. 2015; 102(1):115-122.
23. Smith G I, Atherton P, Reeds D N, et al. Dietary omega-3 fatty acid supplementation increases the rate of muscle protein synthesis in older adults: a randomized controlled trial. *Am J Clin Nutr*. 2011; 93(2):402-412.
24. Gingras A A, White P J, Chouinard P Y, et al. Long-chain omega-3 fatty acids regulate bovine whole-body protein metabolism by promoting muscle insulin signalling to the Akt-mTOR-S6K1 pathway and insulin sensitivity. *J Physiol*. 2007; 579(Pt 1):269-284.
25. Di Girolamo F G, Situlin R, Mazzucco S, Valentini R, Toigo G, Biolo G. Omega-3 fatty acids and protein metabolism: enhancement of anabolic interventions for sarcopenia. *Curr Opin Clin Nutr Metab Care*. 2014; 17(2):145-150.
26. Marine Oils. Drugs and Lactation Database (LactMed) [Internet]. Bethesda (Md.): National Library of Medicine (US); 2006.
27. Trabal J, Forga M, Leyes P, et al. Effects of free leucine supplementation and resistance training on muscle strength and functional status in older adults: a randomized controlled trial. *Clin Interv Aging*. 2015; 10:713-723.
28. Rowlands D S, Nelson A R, Phillips S M, et al. Protein-leucine fed dose effects on muscle protein synthesis after endurance exercise. *Med Sci Sports Exerc*. 2015; 47(3):547-555.
29. Luiking Y C, Deutz N E, Memelink R G, Verlaan S, Wolfe R R. Postprandial muscle protein synthesis is higher after a high whey protein, leucine-enriched supplement than after a dairy-like product in healthy older people: a randomized controlled trial. *Nutr J* 2014; 13:9.
30. Dietz H P, Abbu A, Shek K L. The levator-urethra gap measurement: a more objective means of determining levator avulsion? *Ultrasound Obstet Gynecol*. 2008; 32(7):941-945.
31. Dietz H P, Gamham A P, Rojas R G. Is the levator-urethra gap helpful for diagnosing avulsion? *Int Urogynecol J*. 2016; 27(6):909-913.
32. Kozma B, Larson K, Scott L, et al. Association between pelvic organ prolapse types and levator-urethra gap as measured by 3D transperineal ultrasound. *J Ultrasound Med*. 2018.
33. Afshari P, Dabagh F, Iravani M, Abedi P. Comparison of pelvic floor muscle strength in nulliparous women and those with normal vaginal delivery and cesarean section. *Int Urogynecol J*. 2017; 28(8):1171-1175.
34. Myer E N B, Roem J L, Lovejoy D A, Abernethy M G, Blomquist J L, Handa V L. Longitudinal changes in pelvic floor muscle strength among parous women. *Am J Obstet Gynecol*. 2018.

35. Kamisan Atan I, Shek K L, Furtado G I, Caudwell-Hall J, Dietz H P. The Association Between Levator-Urethra Gap Measurements and Symptoms and Signs of Female Pelvic Organ Prolapse. *Female Pelvic Med Reconstr Surg.* 2016; 22(6):442-446.
36. van Delft K W, Thakar R, Sultan A H, IntHout J, Kluivers K B. The natural history of levator avulsion one year following childbirth: a prospective study. *BJOG.* 2015; 122(9):1266-1273.
37. van Delft K, Sultan A H, Thakar R, Schwertner-Tiepelmann N, Kluivers K. The relationship between postpartum levator ani muscle avulsion and signs and symptoms of pelvic floor dysfunction. *BJOG.* 2014; 121(9):1164-1171; discussion 1172.
38. Dietz H P, Simpson J M. Levator trauma is associated with pelvic organ prolapse. *BJOG.* 2008; 115(8):979-984.
39. Pereira V S, Hirakawa H S, Oliveira A B, Driusso P. Relationship among vaginal palpation, vaginal squeeze pressure, electromyographic and ultrasonographic variables of female pelvic floor muscles. *Braz J Phys Ther.* 2014; 18(5):428-434.
40. Nyhus M, Salvesen K, Volloyhaug I. Association between pelvic floor muscle trauma and contraction in parous women from a general population—a cross sectional study. *Ultrasound Obstet Gynecol.* 2018.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The present invention is further described by the following claims.

The invention claimed is:

1. A method of promoting recovery of pelvic floor muscles in a postpartum female subject, the method comprising administering to the subject a pharmaceutical composition comprising zinc, leucine, and omega-3 fatty acids, wherein the composition is formulated for oral delivery, and wherein administration commences within about 48 hours of vaginal delivery by the subject and continues daily for at least about four weeks.

2. The method of claim 1, wherein administration continues daily for at least about five weeks.

3. The method of claim 1, wherein the recovery comprises reduced instance of weak vaginal squeeze pressure in the subject, compared with the mean vaginal squeeze pressure of a control population of subjects.

4. The method of claim 1, wherein the recovery comprises reduced levator-urethra gap (LUG) in the subject, compared with the mean LUG of a control population of subjects.

5. The method of claim 1, wherein the recovery comprises reduced levator hiatus, compared with the mean levator hiatus of a control population of subjects.

6. The method of claim 1, wherein the recovery comprises an improvement in Pelvic Organ Prolapse Distress Inventory-6 (POPDI-6) standardized scale score of the subject, compared with a baseline POPDI-6 standardized scale score of the subject.

7. The method of claim 1, wherein the pharmaceutical composition comprises a prenatal vitamin.

8. The method of claim 1, wherein the omega-3 fatty acids are selected from docosahexaenoic acid (DHA), eicosapentaenoic acid (EPA), and a combination of DHA and EPA.

9. The method of claim 1, wherein the pharmaceutical composition comprises a total of about 10 mg to about 40 mg zinc.

10. The method of claim 1, wherein the pharmaceutical composition comprises a total of about 2 g to about 10 g leucine.

11. The method of claim 1, wherein the pharmaceutical composition comprises a total of about 500 mg to about 1,500 mg omega-3 fatty acids.

12. The method of claim 1, wherein the pharmaceutical composition comprises a total of about 200 mg to about 750 mg DHA.

13. The method of claim 1, wherein the pharmaceutical composition comprises a total of about 200 mg to about 750 mg EPA.

14. The method of claim 1, wherein the pharmaceutical composition comprises a total of about 250 mg to about 500 mg DHA and a total of about 340 mg to about 590 mg EPA.

15. The method of claim 1, wherein the pharmaceutical composition comprises a total of about 30 mg zinc, a total of about 4 g leucine, a total of about 465 mg EPA, and a total of about 375 mg DHA.

* * * * *